(12) United States Patent
Huang et al.

(10) Patent No.: US 7,374,721 B2
(45) Date of Patent: May 20, 2008

(54) CHIP WITH MEASURING RELIABILITY AND A METHOD THEREOF

(75) Inventors: Yin-Chun Huang, Hsin-Chu (TW); Kuo-Jeng Wang, Kaohsiung (TW)

(73) Assignee: Transpacific IP, Ltd., Taipei (TW)

(*) Notice: Subject to any disclaimer, the term of this patent is extended or adjusted under 35 U.S.C. 154(b) by 679 days.

(21) Appl. No.: 10/726,534

(22) Filed: Dec. 4, 2003

(65) Prior Publication Data

US 2004/0124098 A1   Jul. 1, 2004

(30) Foreign Application Priority Data

Dec. 31, 2002   (TW) ............................. 91138110 A

(51) Int. Cl.
  *B32B 5/02*   (2006.01)
  *B32B 27/04*  (2006.01)
  *B32B 27/12*  (2006.01)
  *B32B 27/00*  (2006.01)
  *G01N 15/06*  (2006.01)

(52) U.S. Cl. .................. 422/82.02; 422/50; 422/56; 422/68.1; 422/82.01; 436/43; 436/91; 436/95; 600/300; 600/347; 600/365

(58) Field of Classification Search .................. 422/50, 422/56, 68.1, 82.01, 82.02; 436/43, 91, 95; 600/300, 347, 365
See application file for complete search history.

(56) References Cited

U.S. PATENT DOCUMENTS

| | | | | |
|---|---|---|---|---|
| 5,282,950 A | * | 2/1994 | Dietze et al. | 204/406 |
| 5,288,636 A | * | 2/1994 | Pollmann et al. | 204/403.14 |
| 5,565,085 A | * | 10/1996 | Ikeda et al. | 205/777.5 |
| 6,349,230 B1 | * | 2/2002 | Kawanaka | 600/347 |
| 6,916,410 B2 | * | 7/2005 | Katsuki et al. | 204/403.05 |
| 7,160,251 B2 | * | 1/2007 | Neel et al. | 600/365 |

* cited by examiner

*Primary Examiner*—Brian Sines
(74) *Attorney, Agent, or Firm*—Stolowitz Ford Cowger LLP

(57) ABSTRACT

A chip with measuring reliability and a method thereof are provided. The present invention serially connects a resistor having a resistance equal to or a little more than a maximum resistance of the chip itself to the resistor $R_s$ of the chip so as to compensate the resistance differences among chips. A noise to signal (N/S) ratio of the chip is decreased, and a measuring reliability of the chip is improved.

21 Claims, 3 Drawing Sheets

CHIP WITH MEASURING RELIABILITY AND A METHOD THEREOF

This Non-provisional application claims priority under 35 U.S.C. § 119(a) on Patent Application No(s). 091138110 filed in Taiwan on Dec. 31, 2002, the entire contents of which are hereby incorporated by reference.

BACKGROUND OF THE INVENTION

1. Field of the Invention

The present invention relates to a biosensor, and more particularly to a biosensor having a chip with measuring reliability and a method for improving measuring reliability thereof.

2. Description of the Prior Art

In recent years, various kinds of biosensors utilizing a specific catalytic action of enzymes have been developed to be used for clinical purposes. Most valuable use of such biosensors may be made in the area of e.g. diabetes treatment where it is vital for patients to keep their blood glucose concentration ("blood sugar level" below) within a normal range. For an inpatient, the blood sugar level can be kept normal under the supervision of the doctor. For an outpatient, self-control of the blood sugar level is an important factor for treatment in lack of doctor's direct supervision.

The self-control of the blood sugar level is achieved through a diet, exercise and medication. These treatments may often be simultaneously employed under the supervision of the doctor. It has been found that the self-control works more effectively when the patient himself is able to check whether or not his blood sugar level is within the normal range.

Recently, blood sugar determining instruments have been used for self-checking of blood sugar level. As shown in FIG. 1, a blood sugar determining instrument mainly includes a main detecting unit 10 and a chip 12 for blood sugar measurement. As shown in FIG. 2, the chip 12 includes a strip-like substrate 122 provided in its front portion with an electrode section 1221. The electrode section 1221 is covered by a reaction layer 124, a spacer 126 and a cover sheet 128. The electrode section 1221 is provided with an operational terminal 1222 and a counterpart terminal 1224 surrounding the operational terminal 1222. The operational terminal 1222 and the counterpart terminal 1224 are electrically connected to lead terminals 1226 and 1228, respectively, which are formed on a base end portion of the strip-like substrate 122. The reaction layer 124, which covers the electrode section 1221, contains potassium ferricyanide and an oxidase such as glucose oxidase.

The blood sugar determining instruments may be used in the following manner. A patient pricks hi or her own skin with e.g. a lancet for oozing blood. Then, the oozed-out blood is caused to touch the tip of the chip 12 plugged into the main detecting unit 10. The blood is partially sucked into the reaction layer 124 by capillary action. The reaction layer 124 disposed above the electrode section 1221, is dissolved by the blood, which starts an enzyme reaction, as the following formula:

D-Glucose + 2Fe(CN)$_6^{3-}$ +

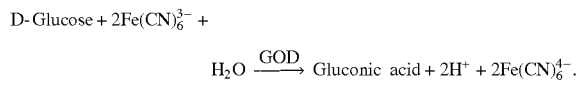

-continued

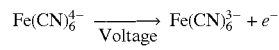

Potassium ferrocyanide is produced in an amount corresponding to the glucose concentration. After a certain period of time, a predetermined voltage $V_{ref}$ is applied on the chip 12 to electrochemically oxidize potassium ferrocyanide to release electrons. A response current is generated and passes through the operational terminal 1222. The response current is proportional to the concentration of potassium ferrocyanide produced by the enzyme reaction or to the concentration of the glucose. Therefore, the blood sugar level can be known by measuring the response current.

FIG. 3 is a schematic diagram of a control circuit of the blood sugar determining instrument of FIG. 1, in which the electrode section 1221 of the chip 12 can be regarded as a resistor $R_s$. The voltage $V_{ref}$ to be applied can be provided by a battery. The response current I generated by the chip 12 is converted to an output voltage $V_{out}$ by a current/voltage converter 30 having an amplification resistance $R_f$. The output voltage $V_{out}$ is represented by the formula (I):

$$V_{out}=(1+R_f/R_s)V_{ref} \qquad (I),$$

A microprocessor (not shown) processes the output voltage $V_{out}$ through the analog to digital converter (not shown), and accordingly calculates the glucose concentration of the blood sample. A reading of the glucose concentration is displayed on a display such as a liquid crystal display (LCD) (not shown).

However, the resistance difference among the substrates 122 (or the chips 12) is caused during the manufacturing process thereof. In general, the resistance of the resistor $R_s$ of the substrate 122 is in the range of 2K to 4K. Referring to the formula (I), due to the resistance difference of the substrates 122, the output voltage $V_{out}$ caused by each chip 12 in response to the same blood sample is different. As a result, different chips 12 monitor different glucose concentrations for the same blood sample. Therefore, the resistance difference of the resistor $R_s$ of the substrate 122 reduces the measuring reliability of the chip 12.

Accordingly, it is an intention to provide means for improving measuring reliability of the chip, which can resolve the problem encountered by the conventional biosensor.

SUMMARY OF THE INVENTION

It is one objective of the present invention to provide a chip with measuring reliability, which serially connecting a resistor having a resistance equal to or a little more than a maximum resistance of the chip itself to the chip to compensate resistance difference among the chips. The measuring reliability of the chip thus can be improved.

It is another objective of the present invention to provide a chip with measuring reliability, which can increase measuring accuracy of a content of a specific component of a specimen.

It is a further objective of the present invention to provide a method for improving measuring reliability of a chip, which extends a longitudinal dimension of each of an operational electrode and a counterpart electrode of the chip or widens both of them in order to serially connect a resistor to the chip. The resistance difference among the chips thus can be reduced and the measuring reliability of the chip can be improved. The present method is simple and does not need additional manufacturing steps. The purpose of cost down can be obtained.

In order to achieve the above objectives of this invention, the present invention provides a chip with measuring reliability, which includes a substrate, a reaction layer, a spacer, and a cover. The substrate has a first section and a second section. An operational electrode and a counterpart electrode spaced-apart each other are formed on the first section, and a resistor is connected with the operational electrode in series. A first terminal and a second terminal are formed on the second section. The operational electrode and the counterpart electrode constitute a resistor $R_s$, and the resistance of the resistor serially connected with the operational electrode is equal to or a little more than a maximum resistance of the resistor $R_s$. The operational electrode and the counterpart electrode respectively electrically connect to the first terminal and the second terminal. The first terminal and the second terminal electrically connect to a main detecting unit of a biosensor. The main detecting unit is used for detecting a response current passing through the operational electrode. The response current is generated in response to a specific component of a specimen applied on the chip. The reaction layer is placed above the first section of the substrate for covering the operational electrode and the counterpart electrode. The reaction layer includes a redox mediator and an enzyme, the redox mediator and the specific component of the specimen applied on the chip proceeds an electrochemical reaction under catalysis of the enzyme. The spacer is placed above the reaction layer, the spacer has a passage formed in an end thereof corresponding to the reaction layer. A cover is placed above the spacer, the cover has an opening over the passage of the spacer in order for the specimen sucked into the reaction layer through the opening and the passage. The present invention serially connects a resistor having a resistance equal to or a little more than a maximum resistance of the chip itself to the chip to compensate resistance difference among the chips. The noise to signal (N/S) ratio of the chip can be reduced, thus improving the measuring reliability of the chip and the measuring accuracy of the concentration of the specific component.

BRIEF DESCRIPTION OF THE DRAWINGS

The objectives and features of the present invention as well as advantages thereof will become apparent from the following detailed description, considered in conjunction with the accompanying drawings.

DESCRIPTION OF THE PREFERRED EMBODIMENTS

Figure 1:
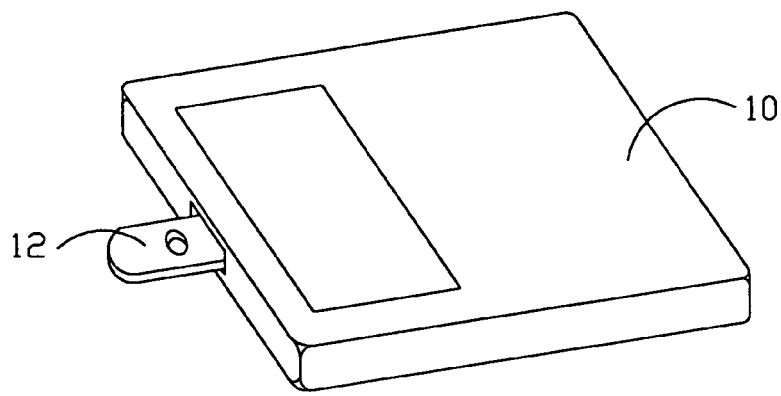
FIG. 1 is a schematic perspective view of a conventional blood sugar determining instrument.
Figure 2:
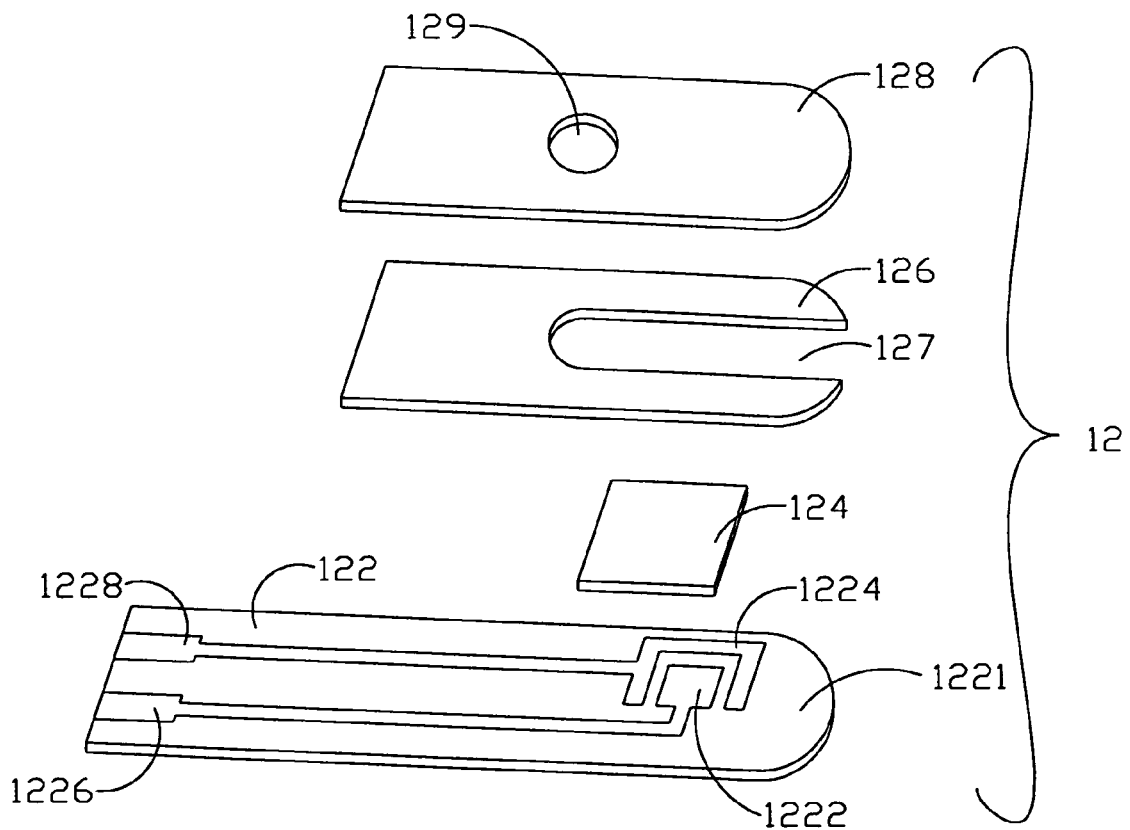
FIG. 2 is an exploded view of a chip of the conventional blood sugar determining instrument of FIG. 1.
Figure 3:
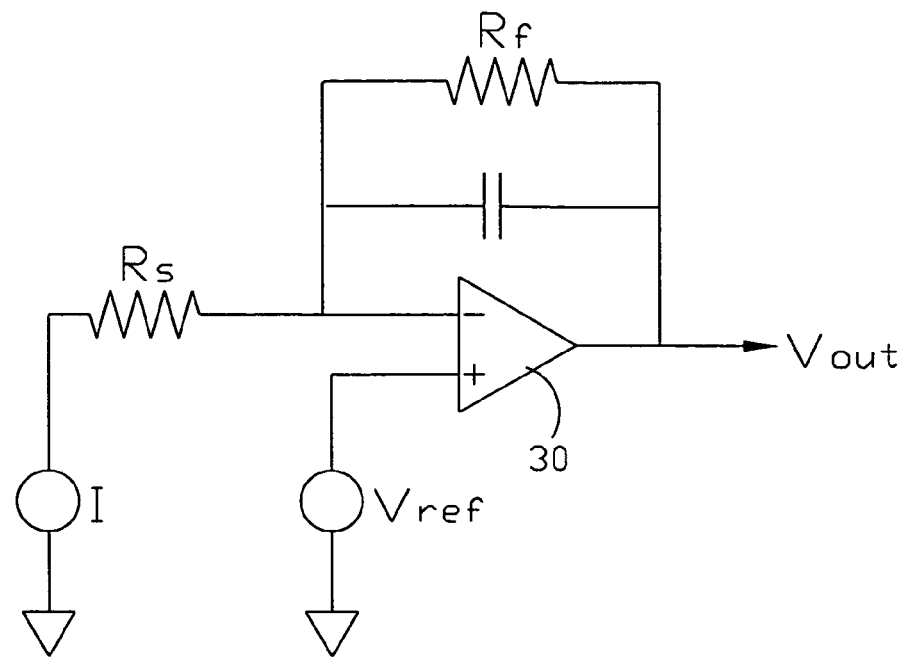
FIG. 3 is a schematic diagram of a control circuit of the conventional blood sugar determining instrument of FIG. 1.

The most elements of a biosensor utilized in the present invention are substantially the same with those of the blood sugar determining instrument of FIG. 1 and FIG. 2, mainly including a chip and a main detecting unit. The chip is plugged into the main detecting unit before using the biosensor. Then, a specimen is applied on the chip, and the main detecting unit detects a response current generated in response to a specific component of the specimen. The main detecting unit determines a concentration of the specific component based on the response current. The chip of the present invention includes a substrate, a reaction layer, a spacer and a cover. The substrate of the chip has a first section and a second section, an operational electrode and a counterpart electrode spaced-apart each other are formed on the first section. The response current generated in response to the specific component of the specimen passes through the operational electrode. Therefore, the operational electrode and the counterpart electrode can be considered as a resistor $R_s$. In general, the resistance of the resistor $R_s$ is in the range of 2K to 4K. There is resistance difference present among the chips. The present invention serially connects a resistor having a resistance equal to or a little more than a maximum resistance of the resistor $R_s$ of the chip itself to the chip in order for compensating the resistance difference among the chips. For example, a resistor having a resistance of 4K is serially connected to the chip so that the resistance difference among the chips becomes in the range of 6K to 8K. As a consequence, the signal to noise (S/N) ratio of the chip becomes 1K/7K from 1K/3K. The measuring reliability of the chip is thus improved.

A first terminal and a second terminal are formed on the second section of the chip of the present invention. The operational electrode and the counterpart electrode respectively electrically connect to the first terminal and the second terminal. The first terminal and the second terminal electrically connect to the main detecting unit in order for the main detecting unit detecting the response current passing through the operational electrode, which is generated in response to the specific component of the specimen. The reaction layer of the chip is placed above the first section of the substrate for covering the operational electrode and the counterpart electrode. The reaction layer includes a redox mediator and an enzyme. The redox mediator and the specific component of the specimen applied on the chip proceed an electrochemical reaction under catalysis of the enzyme. The specific component of the specimen to be detected depends on the type of the enzyme of the reaction layer. For example, when the reaction layer contains potassium ferricyanide as the redox mediator and glucose oxidase as the enzyme, the chip can be used to detect a glucose concentration of a blood sample. When the reaction layer contains potassium ferricyanide as the redox mediator and lactate oxidase as the enzyme, the chip can be used to detect a concentration of lactic acid of saliva.

The spacer is placed above the reaction layer, and a passage is formed on an end thereof corresponding to the reaction layer. The cover is placed above the spacer, and an opening is formed in the cover above the passage in order for the specimen sucked into the reaction layer through the opening and the passage. The reaction layer is dissolved by the specimen to start an enzyme-catalytic electrochemical reaction.

Figure 4:
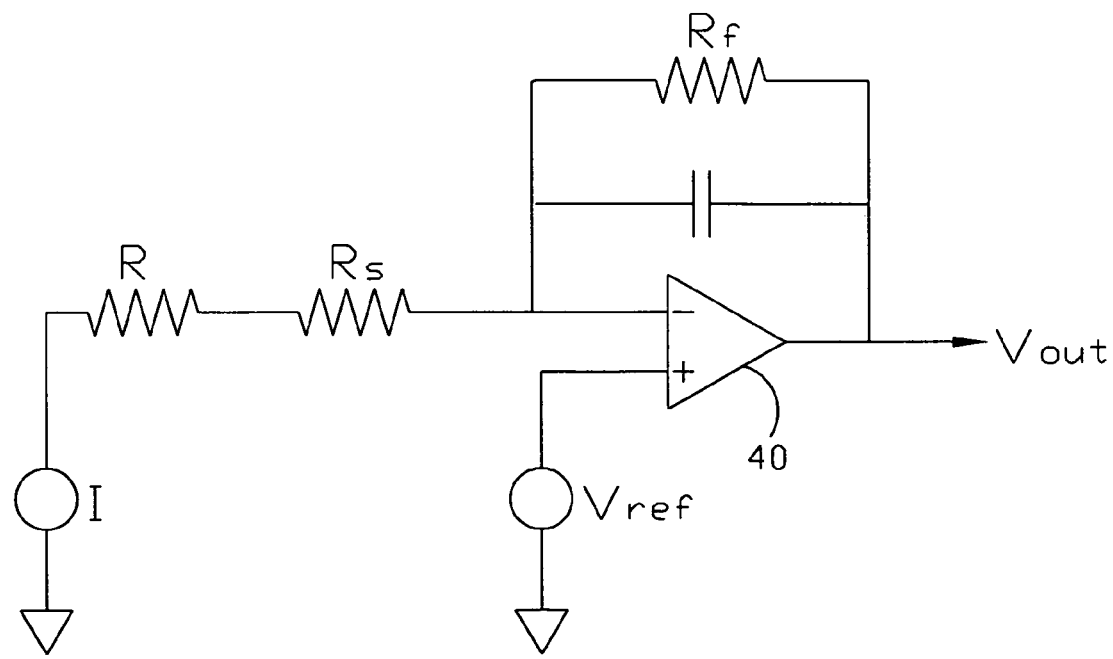
FIG. 4 is a schematic diagram of partly control circuit of a biosensor of the present invention.

FIG. 4 is a schematic diagram of partly control circuit of the biosensor of the present invention. The chip itself has a resistor $R_s$ and a resistor R having a resistance equal to or a little more than a maximum resistance of the resistor $R_s$ serially connects to the resistor $R_s$ of the chip. The specimen applied on the chip is sucked into the reaction layer, and dissolving it. After a period of time, the enzyme-catalytic electrochemical reaction between the redox mediator and the specific component of the specimen completes, the reduced redox mediator becomes electron carriers, accumulating in the area of the first section of the substrate. Afterward, a voltage $V_{ref}$, for example supplied by a battery, is applied on the operational electrode of the first section of the substrate in order that the reduced redox mediator releases electrons to cause a response current I passing through the operational electrode. The response current I is converted to an output voltage $V_{out}$ by a current/voltage converter 40, having an amplification resistor $R_f$. The main detecting unit determines a concentration of the specific component of the specimen in accordance with the output voltage $V_{out}$. As shown in FIG. 4, the resistor R, serially connecting to the resistor $R_s$ of the chip itself, has a resistance equal to or a little more than the maximum resistance of the resistor $R_s$ of the chip so as to compensate the resistance difference among the chips. The signal to noise (S/N) ratio of the chip is reduced and the measuring reliability and accuracy of the chip are improved.

The chip with measuring reliability provided by the present invention will be described in detail in accordance with preferred embodiments of the present invention with reference to accompanying drawings.

Figure 5:
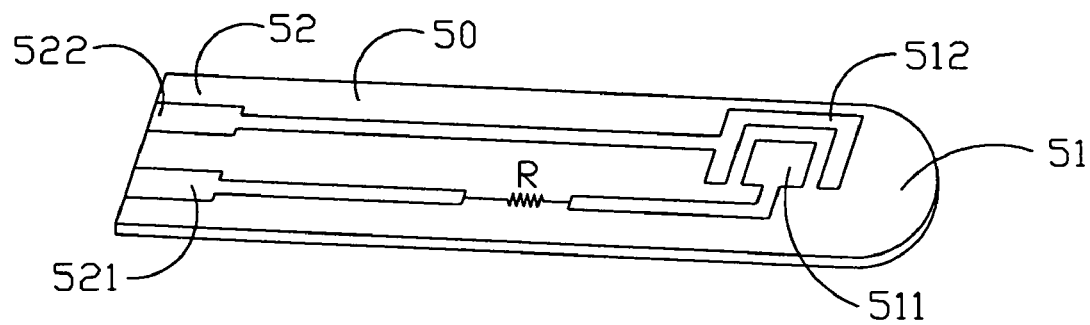
FIG. 5 is a schematic perspective view of a substrate of a chip according to a first preferred embodiment of the present invention.

FIG. 5 is a schematic perspective view of a strip-like substrate 50 of the chip of the present invention according to a first preferred embodiment. A first section 51 of the strip-like substrate 50 has a strip-like operational electrode 511 and a strip-like counterpart electrode 512 spaced-apart each other formed thereon. A resistor R is serially connected to the strip-like operational electrode 511. The second section 52 has a first terminal 521 and a second terminal 522 formed thereon. The strip-like operational electrode 511 and the strip-like counterpart electrode 512 respectively electrically connect to the first terminal 521 and the second terminal 522. The resistance of the resistor R is equal to or a little more than the maximum resistance of the resistor $R_s$ constituted by the strip-like operational electrode 511 and the strip-like counterpart electrode 512. The strip-like operational electrode 511 and the strip-like counterpart electrode 512 preferably are formed of the same conductive material, such as palladium (Pd), platinum (Pt), gold (Au), silver (Ag), carbon (C), titanium (Ti) and copper (Cu). The strip-like operational electrode 511, the strip-like counterpart electrode 512, the first terminal 521 and the second terminal 522 can be formed on the substrate 50 by a screen printing technology.

Figure 6:
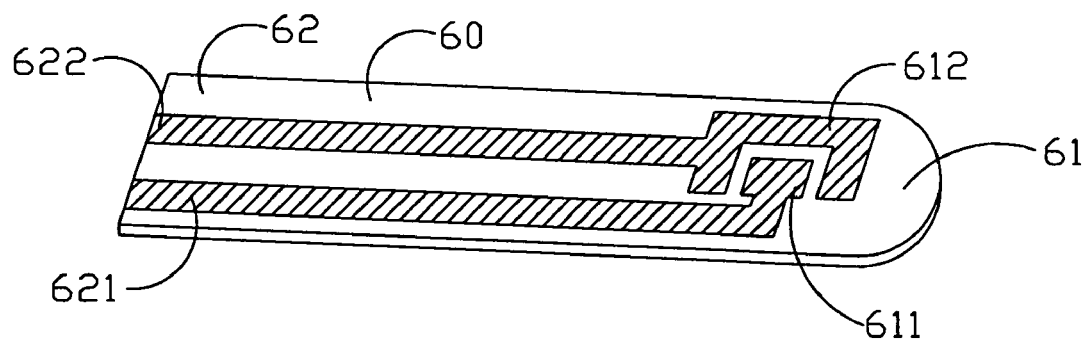
FIG. 6 is a schematic perspective view of a substrate of a chip according to a second preferred embodiment of the present invention.

FIG. 6 is a schematic perspective view of a strip-like substrate 60 of the chip of the present invention according to a second preferred embodiment of the present invention. A first section 61 of the strip-like substrate 60 has a widened strip-like operational electrode 611 and a widened strip-like counterpart electrode 612 formed thereon. A second section 62 of the strip-like substrate 60 has a first terminal 621 and a second terminal 622 formed thereon. The widened strip-like operational electrode 611 and the widened strip-like counterpart electrode 612 respectively electrically connect to the first terminal 621 and the second terminal 622. In the second preferred embodiment, the present invention widens the strip-like operational electrode 611 and the strip-like counterpart electrode 612 to increase the resistance of the chip itself, which is equivalent to serially connecting a resistor R to the chip itself. The resistance difference among the chips is compensated by way of controlling the width of the strip-like operational electrode 611 and the strip-like counterpart electrode 612. The strip-like operational electrode 611 and the strip-like counterpart electrode 612 substantially have the same size, dimension, and conductive material, for example, palladium (Pd), platinum (Pt), gold (Au), silver (Ag), carbon (C), titanium (Ti) and copper (Cu). The strip-like operational electrode 611, the strip-like counterpart electrode 612, the first terminal 621 and the second terminal 622 can be formed on the substrate 60 by a screen printing technology.

Figure 7:
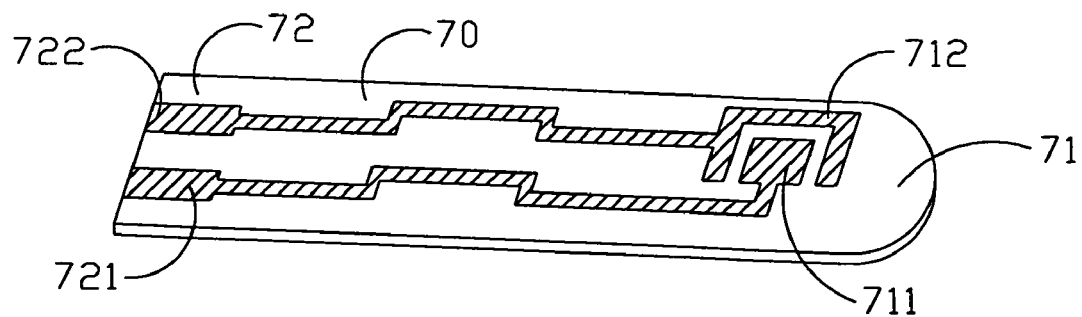
FIG. 7 is a schematic perspective view of a substrate of a chip according to a third preferred embodiment of the present invention.

FIG. 7 is a schematic perspective view of a strip-like substrate 70 of the chip of the present invention according to a third preferred embodiment of the present invention. A first section 71 of the strip-like substrate 70 has a bent strip-like operational electrode 711 and a bent strip-like counterpart electrode 712 formed thereon. A second section 72 of the strip-like substrate 70 has a first terminal 721 and a second terminal 722 formed thereon. The bent strip-like operational electrode 711 and the bent strip-like counterpart electrode 712 respectively electrically connect to the first terminal 721 and the second terminal 722. In the third preferred embodiment, the present invention extends a longitudinal dimension of the strip-like operational electrode 711 and the strip-like counterpart electrode 712 to increase the resistance of the chip itself, which is equivalent to serially connecting a resistor R to the chip. For example, under maintaining the original longitudinal dimension of the substrate 70, forming the bent strip-like operational electrode 711 and the bent strip-like counterpart electrode 712 to increase the resistance of the chip. The resistance difference among the chips can be compensated by way of controlling the longitudinal dimension of the bent strip-like operational electrode 711 and the bent strip-like counterpart electrode 712. The bent strip-like operational electrode 711 and the bent strip-like counterpart electrode 712 substantially have the same size, dimension, and conductive material, for example, palladium (Pd), platinum (Pt), gold (Au), silver (Ag), carbon (C), titanium (Ti) and copper (Cu). The bent strip-like operational electrode 711, the bent strip-like counterpart electrode 712, the first terminal 721 and the second terminal 722 can be formed on the substrate 70 by a screen printing technology.

The present method for improving measuring reliability of the chip is simple and does not need additional manufacturing steps. The purpose of cost down can be attained.

The embodiments are only used to illustrate the present invention, not intended to limit the scope thereof. Many modifications of the embodiments can be made without departing from the spirit of the present invention.

What is claimed is:

1. A biosensor measuring instrument, comprising:
a substrate having a first section and a second section, an operational electrode and a counterpart electrode spaced-apart from each other and formed on the first section, a first resistor connected with the operational electrode in series, and a first terminal and a second terminal formed on the second section; wherein the operational electrode and the counterpart electrode constitute a second resistor $R_s$, and the resistance of the first resistor is equal to or greater than a maximum resistance of the second resistor $R_s$, the operational electrode and the counterpart electrode respectively electrically connected to the first terminal and the second terminal for detecting a response current passing through the operational electrode; and
a reaction layer at the first section of the substrate for at least partially covering the operational electrode and the counterpart electrode, wherein the response current is generated in response to a voltage applied to the operational electrode and a specific component of a specimen that reacts with the reaction layer.

2. The instrument of claim 1, wherein the operational electrode and the counterpart electrode are comprised of the same conductive material.

3. The instrument of claim 1, wherein the reaction layer comprises an enzyme type, and wherein the specific component of the specimen to be detected depends on the enzyme type of the reaction layer.

4. The instrument of claim 3, wherein the reaction layer is configured to react with a glucose concentration of a blood sample.

5. The instrument of claim 3, wherein the reaction layer is configured to react with a lactic acid concentration of saliva.

6. The instrument of claim 1, wherein the reaction layer includes a redox mediator, the redox mediator and specific component of the specimen applied on the chip proceeding an electrochemical reaction under catalysis of the enzyme.

7. The instrument of claim 1, further comprising a spacer over at least a portion of the reaction layer.

8. The instrument of claim 7, further comprising a cover over the spacer, the cover having an opening through which the specimen can be introduced.

9. A biosensor measuring instrument comprising:
a substrate having a first section and a second section;
a first lead terminal and a second lead terminal each formed on the second section of the substrate;
a counterpart terminal electrode formed on the first section of the substrate, the counterpart terminal electrode electrically connected to the second lead terminal;
an operational terminal electrode formed on the first section of the substrate, the operational terminal electrode electrically connected to the first lead terminal, wherein the operational terminal electrode and the counterpart terminal electrode constitute a first resistor having a first resistance;
a second resistor on the substrate, the second resistor having a second resistance substantially equal to or greater than the first resistance of the first resistor, wherein the second resistor is serially connected with the operational terminal electrode; and
a reaction layer covering the operational terminal electrode and counterpart terminal electrode, wherein the reaction layer is configured to react with a specimen to modify a response current passing through the operational terminal electrode.

10. The instrument of claim 9, wherein the second resistor includes a resistor electrically connected between the operational terminal electrode and the first lead terminal.

11. The instrument of claim 9, wherein the second resistor includes a widened portion of the counterpart terminal electrode and a widened portion of the operational terminal electrode.

12. The instrument of claim 9, wherein the second resistor includes a bent strip portion of the counterpart terminal electrode and a bent strip portion of the operational terminal electrode.

13. The instrument of claim 12, wherein the bent strip portion of the counterpart terminal electrode is substantially the same dimension as the bent strip portion of the operational terminal electrode.

14. A biosensor measuring instrument for determining the blood sugar level of a specimen, the instrument comprising:
a substrate having an operational terminal electrode and a counterpart terminal electrode respectively connected to first and second lead terminals;
a reaction layer including a redox mediator and an enzyme and covering the operational terminal electrode and counterpart terminal electrode, wherein a current passing through the operational terminal electrode is determined in part according to a reaction of the reaction layer with a specimen;
a spacer disposed over the reaction layer, and a cover disposed over the spacer, wherein the operational terminal electrode and the counterpart terminal electrode constitute a first resistor having a first resistance; and
a second resistor serially connected with the operational terminal electrode, the second resistor having a second resistance substantially equal to or greater than the first resistance of the first resistor.

15. The instrument of claim 14, wherein the second resistor includes a resistor electrically connected between the operational terminal electrode and the first lead terminal.

16. The instrument of claim 14, wherein the second resistor includes a widened portion of the counterpart terminal electrode and a widened portion of the operational terminal electrode.

17. The instrument of claim 14, wherein the second resistor includes a bent strip portion of the counterpart terminal electrode and a bent strip portion of the operational terminal electrode.

18. The instrument of claim 17, wherein the bent strip portion of the counterpart terminal electrode is substantially the same dimension as the bent strip portion of the operational terminal electrode.

19. A biosensor measuring instrument comprising:
a substrate having a first section and a second section;
a first lead terminal and a second lead terminal each formed on the second section of the substrate;
a reactive means covering the first section of the substrate, wherein a response current passing between the first and second lead terminals is determined in part according to a reactive state of the reactive means;
a first resistive means on the first section of the substrate for providing a first resistance between the first and second lead terminal; and
a second resistive means on the substrate for providing a second resistance substantially equal to or greater than the first resistance of the first resistor, wherein the second resistive means is serially connected with the first resistive means.

20. The biosensor measuring instrument of claim 19, wherein the reactive state of the reactive means varies according to a specimen being measured.

21. The biosensor measuring instrument of claim 14, wherein the second resistor is serially connected between the first resistor and the lead terminal.

* * * * *

UNITED STATES PATENT AND TRADEMARK OFFICE
CERTIFICATE OF CORRECTION

PATENT NO. : 7,374,721 B2
APPLICATION NO. : 10/726534
DATED : May 20, 2008
INVENTOR(S) : Yin-Chun Huang et al.

Page 1 of 1

It is certified that error appears in the above-identified patent and that said Letters Patent is hereby corrected as shown below:

At column 7, line 19, after "and" insert -- the --.

Signed and Sealed this

Twenty-fifth Day of August, 2009

David J. Kappos
*Director of the United States Patent and Trademark Office*